(12) United States Patent
Duckert et al.

(10) Patent No.: US 7,127,371 B2
(45) Date of Patent: Oct. 24, 2006

(54) CUSTOMIZED MEDICAL EQUIPMENT PREVENTATIVE MAINTENANCE METHOD AND SYSTEM

(75) Inventors: David Wayne Duckert, Menomonee Falls, WI (US); Howard Jerome Anstedt, Milwaukee, WI (US)

(73) Assignee: GE Medical Systems Information, Milwaukee, WI (US)

(*) Notice: Subject to any disclaimer, the term of this patent is extended or adjusted under 35 U.S.C. 154(b) by 81 days.

(21) Appl. No.: 10/681,631

(22) Filed: Oct. 8, 2003

(65) Prior Publication Data

US 2005/0080596 A1    Apr. 14, 2005

(51) Int. Cl.
*G06F 19/00*    (2006.01)
(52) U.S. Cl. ............... 702/179; 702/179; 702/181; 702/184; 702/187; 700/21; 700/28; 700/30; 714/47; 361/1; 340/457.4; 324/383
(58) Field of Classification Search ............... 702/179, 702/181–184, 187; 700/21, 28, 30; 714/47, 714/732; 361/1, 93.2; 340/457.4
See application file for complete search history.

(56) References Cited

U.S. PATENT DOCUMENTS

| | | | | |
|---|---|---|---|---|
| 4,284,972 A | * | 8/1981 | Chiu et al. | 340/457.4 |
| 4,539,632 A | * | 9/1985 | Hansen et al. | 700/14 |
| 5,030,905 A | * | 7/1991 | Figal | 324/760 |
| 5,177,684 A | * | 1/1993 | Harker et al. | 701/117 |
| 6,108,800 A | * | 8/2000 | Asawa | 714/47 |
| 2004/0117153 A1 | * | 6/2004 | Siegel et al. | 702/183 |
| 2005/0218925 A1 | * | 10/2005 | Miao et al. | 324/767 |

OTHER PUBLICATIONS

Campean et al., 'Camshaft Timing-Belt Reliability Modeling', Jan. 2001, IEEE Article, pp. 377-383.*
Gullo, 'In Service Reliability Assessment and Top-Down Approach Provides Alternative Reliability Prediction Method', Jan. 1999, IEEE Article, pp. 365-377.*
Kececioglu et al., 'The Modified Gompertz Reliability-Growth Model', 1994, IEEE Article, pp. 160-165.*

* cited by examiner

*Primary Examiner*—Marc S. Hoff
*Assistant Examiner*—Elias Desta
(74) *Attorney, Agent, or Firm*—Fletcher Yoder

(57) ABSTRACT

A technique is provided for determining service intervals for devices, such as medical equipment. Data related to a device is collected and compared to data from a population of like devices. A service interval may be calculated based on the comparison. The data regarding the population of like devices may be raw quantitative or qualitative data or may be processed data, such as may be used to graph the reliability of the device as a function of some variable such as usage or age, i.e. a reliability curve. The data may representative of the device as a whole or one or more components of the device. Multiple service intervals may be generated for a single device by calculating a service interval for each data source, such as a component or subset of components, of the device. An optimal service interval may then be selected. In addition, the technique may be applied for selection of a service interval for more than one device.

50 Claims, 7 Drawing Sheets

CUSTOMIZED MEDICAL EQUIPMENT PREVENTATIVE MAINTENANCE METHOD AND SYSTEM

BACKGROUND OF THE INVENTION

Embodiments of the present invention relate generally to preventative maintenance of devices. Particularly, one embodiment relates to a technique for determining service intervals for medical devices.

In the field of medical equipment, such as imaging systems, patient monitors, and other types of diagnostic and monitoring equipment, regular maintenance is important for providing a high degree of reliability and operability. This equipment may require periodic servicing of components that may wear, be consumed, or become uncalibrated. It is common in the field of medical equipment servicing to provide for both "as needed" servicing (i.e. in response to service requests), and for regular servicing to ensure optimum performance and efficiency of equipment throughout medical institutions.

Current approaches for servicing medical equipment include regular service calls, typically based upon contractual arrangements between service providers and medical institutions. The service providers commonly schedule either on-site service visits or remote servicing, or both, on a regular timed basis. The intervals between such visits are generally determined in rather empirical fashions, however, and may vary widely between service providers, institutions, contracts, regions, and so forth, even for similar types of equipment or usage patterns.

While vital to the proper functioning of hospitals, the regular maintenance of their medical equipment is both time-consuming and costly. Under previous regulation of these institutions, regular maintenance checks of the equipment were required, regardless of whether a device actually needed repair. The regulatory environment has since changed, however, to provide hospitals greater flexibility in developing maintenance schedules. This freedom allows hospitals to extend the time between service visits for a number of devices, resulting in lower maintenance expenses and, thereby, a lower cost of ownership. However, hospitals must still produce maintenance plans that can be justified to patients and to the regulatory authorities.

There is, therefore, a need in the field of medical equipment servicing for an improved technique for determining service intervals for such equipment that would be more closely coupled to the actual need for servicing. There is a particular need for a technique that would permit service intervals to be based upon some criteria or criterion other than simple time intervals.

BRIEF DESCRIPTION OF THE INVENTION

The present technique provides a novel technique for determining service intervals for medical equipment. The technique is applicable to a wide range of equipment, but is particularly well suited to sensitive and specialized equipment, such as diagnostic imaging systems and patient monitors. It should be noted, however, that the technique may be employed to determine service intervals for equipment outside of the medical field, such as in non-medical imaging systems (for part inspection, baggage inspection, quality control, etc.) and complex machinery. The present technique may be practiced with any device that requires periodic maintenance.

In accordance with a first aspect of the technique, a method for determining a service interval for a device is provided. The method includes steps for collecting data from the device and comparing the data to a reliability curve. This reliability curve is based on a population of similar devices, and may be representative of whole devices, or may represent the reliability of individual components of the device population. The method then provides for calculating a service interval based upon the relation between the data collected and the associated reliability curve.

In accordance with another aspect of the technique, a method is provided for selecting one service interval for a device from a plurality of intervals generated by the previous method. This method allows the selection of an optimal service interval based upon operational data and other information, which may or may not be directly related to the device. Numerous diverse factors may be considered in this selection process in addition to operational data. These other factors may include device-specific information such as the age of the device, the operating environment, the workflow and traffic level associated with the location of the device, the criticality associated with the device, and the repair history of the particular device. Other information not directly related to the device such as contractual service agreements or institutional policy may also be considered in applying the present technique.

In accordance with a further aspect of the technique, a method is provided for determining service intervals for equipment, in which steps are provided for collecting data from a plurality of devices via a network, comparing the data collected to an associated reliability curve for each device or component, and calculating service intervals based on this comparison. This method permits coordination of equipment servicing, possibly reducing the number of visits by repair technicians by having multiple pieces of equipment serviced on the same trip. Systems and computer programs that afford functionality of the type defined by such methods are also provided by the present technique.

DETAILED DESCRIPTION OF SPECIFIC EMBODIMENTS

Figure 1:
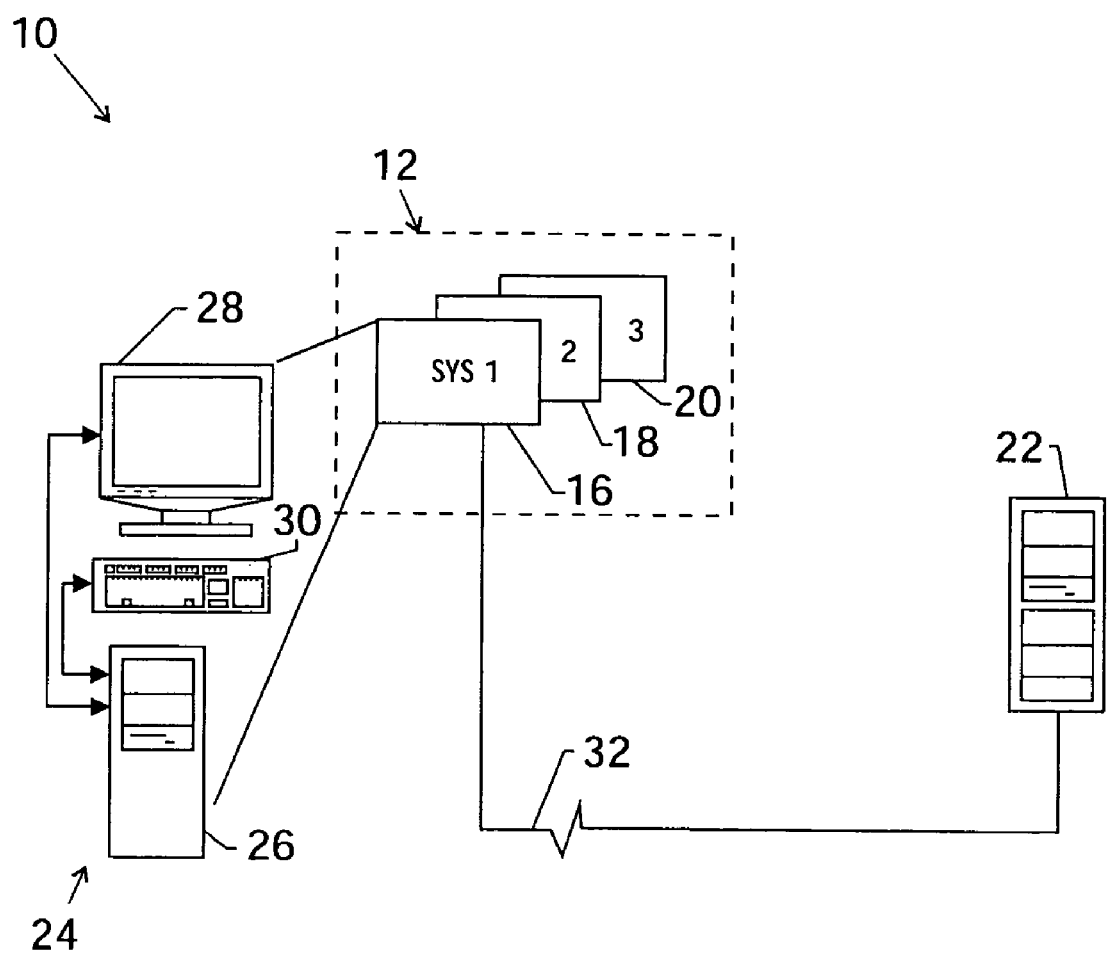
FIG. 1 is a diagrammatical representation of an exemplary system for determining optimal service intervals in accordance with aspects of the present technique.

Turning now to the drawings, and referring first to FIG. 1, a system capable of determining service intervals for devices is illustrated and designated generally by the reference numeral 10. While scheduling system 10 may be utilized to determine a service interval for a wide range of devices, it is particularly well suited to providing service intervals for medical equipment, including medical diagnostic imaging systems and patient monitoring systems. Such systems are often complex and generally require high degrees of reliability, accuracy, and precision. In addition, such systems may present scheduling difficulties due to near constant use or the need to maintain availability. These various factors, alone or in combination, contribute to the service scheduling challenges posed by many types of medical equipment.

Such challenges are addressed in the present technique. In accordance with aspects of the technique, service intervals may be generated and selected based on operational data for the device, an associated reliability curve, and other data related to the device. Moreover, as described in detail below, usage-scheduling aspects of the technique permit recasting of maintenance schedules as a function of changing usage, thereby avoiding unnecessary maintenance while ensuring that maintenance is customized by the actual usage of the equipment.

In the embodiment of FIG. 1, scheduling system 10 is illustrated as a device group 12 networked with a server 22, which may be local or remote to device group 12. Additional device groups 12 may, of course, be similarly linked to scheduling system 10 if desired. Each group 12, in turn, may include a range of equipment, designated herein as maintained systems 16, 18, and 20, which may comprise medical systems such as monitoring or imaging systems. The individual maintained systems 16, 18, and 20 may be remote from one another, such as at different physical locations in an institution, in different departments, on different floors, and so forth.

Maintained systems 16, 18, and 20 typically include an operator interface station 24, either integral to or remote from the maintained system 16, 18, or 20. Operator interface station 24 may control some or all of the functions of the equipment comprising the maintained system 16, 18, or 20 and may also be used to view maintenance schedules of the devices within scheduling system 10. Interface stations 24 may include one or more general purpose or application specific computers 26 or processor-based interfaces, including memory for storing data collection routines and the resulting data that can be accessed by scheduling system 10. Alternatively, such data may be stored within memory resident on the equipment comprising the maintained system 16, 18, or 20 and accessed directly therefrom. System interface station 24 may include a monitor 28 or other visual display and one or more input devices 30 that may be used for viewing and inputting information regarding scheduling system 10, as described below.

Scheduling system 10 may include a number of components to carry out the functionality described below. Such components may comprise any suitable computer hardware, software or firmware, including elements located at a single location and elements widely dispersed from one another. As will be appreciated by those skilled in the art, any suitable circuitry, such as modems, servers, firewalls, VPN's and so forth may be included within the network.

In a present embodiment, scheduling system 10 includes a network of components configured to exchange data with systems 16, 18, and 20 of group 12. Such data may include various operational parameters of the systems, which will vary depending upon the equipment type, the manufacturer, the physical nature of the operation of the equipment, and so forth. Systems 16, 18, and 20, may measure such operational data through various means, and may incorporate one or more of the following: a run time meter, a cycle counter, a continuous system monitor, and a self-test monitor. The present technique is not dependent on any particular measurement and may be practiced with or without these specific measuring devices.

Additional data may be exchanged with server 22. Server 22 may contain data specific to the devices of systems 16, 18, and 20, such as the age of devices within the systems, the workflow and traffic level associated with the device locations, the criticality associated with the devices, the repair history of particular devices, and the environmental conditions around the devices. Server 22 also may contain data relating to a population of similar devices, such as repair histories for the population or reliability curves for devices (or their individual components). Data regarding a population of devices does not have to be so comprehensive as to include data on every like device made by the same manufacturer; a representative sample may be sufficient for purposes of the present technique.

As described more fully below, collected data may include raw, partially processed or processed data, and may represent various parameters of specific devices or general observations about all similar devices. When planned maintenance is to be performed on a usage basis, indications of the degree of usage, and therefore the appropriate timing for maintenance, may be provided by the collected data itself, or by data derived from the collected data. For example, as described below, maintenance of a CT imaging system may be appropriately scheduled based upon revolutions of a gantry assembly, while collected data may reflect more fundamental data that is present in the CT system and that can be related to gantry revolutions by known relationships programmed into the system.

The entire scheduling system 10 may then communicate with the various maintained systems 16, 18, and 20 via links to a network 32, over which it may transmit schedules and collect the data required for scheduling maintenance. Various algorithms may be implemented within scheduling system 10 to weigh different variables in determining an appropriate service interval. The calculated service intervals, along with collected data, system identifying data, and other data, may then be stored within a suitable memory in scheduling system 10 at a location proximate device group 12 (such as within the devices comprising systems 16, 18, and 20, or within computer 26 of interface station 24) or at a location remote from device group 12, such as at server 22 of scheduling system 10.

As mentioned above, the present technique is well suited for determining service intervals for complex medical equipment, such as medical diagnostic imaging systems or patient monitoring systems. By way of example, FIGS. 2–5 illustrate generic and certain specific modalities of medical equipment with which the current technique may be implemented. The technique disclosed herein, however, is not limited to the specific applications described, but may be applied in other contexts as well. For instance, the technique may be employed with imaging devices outside the medical field, such as in part inspection, baggage inspection, and quality control. Indeed, the technique may be employed with any device undergoing routine, regular, or scheduled maintenance in order to maintain reliability or functionality.

Figure 2:
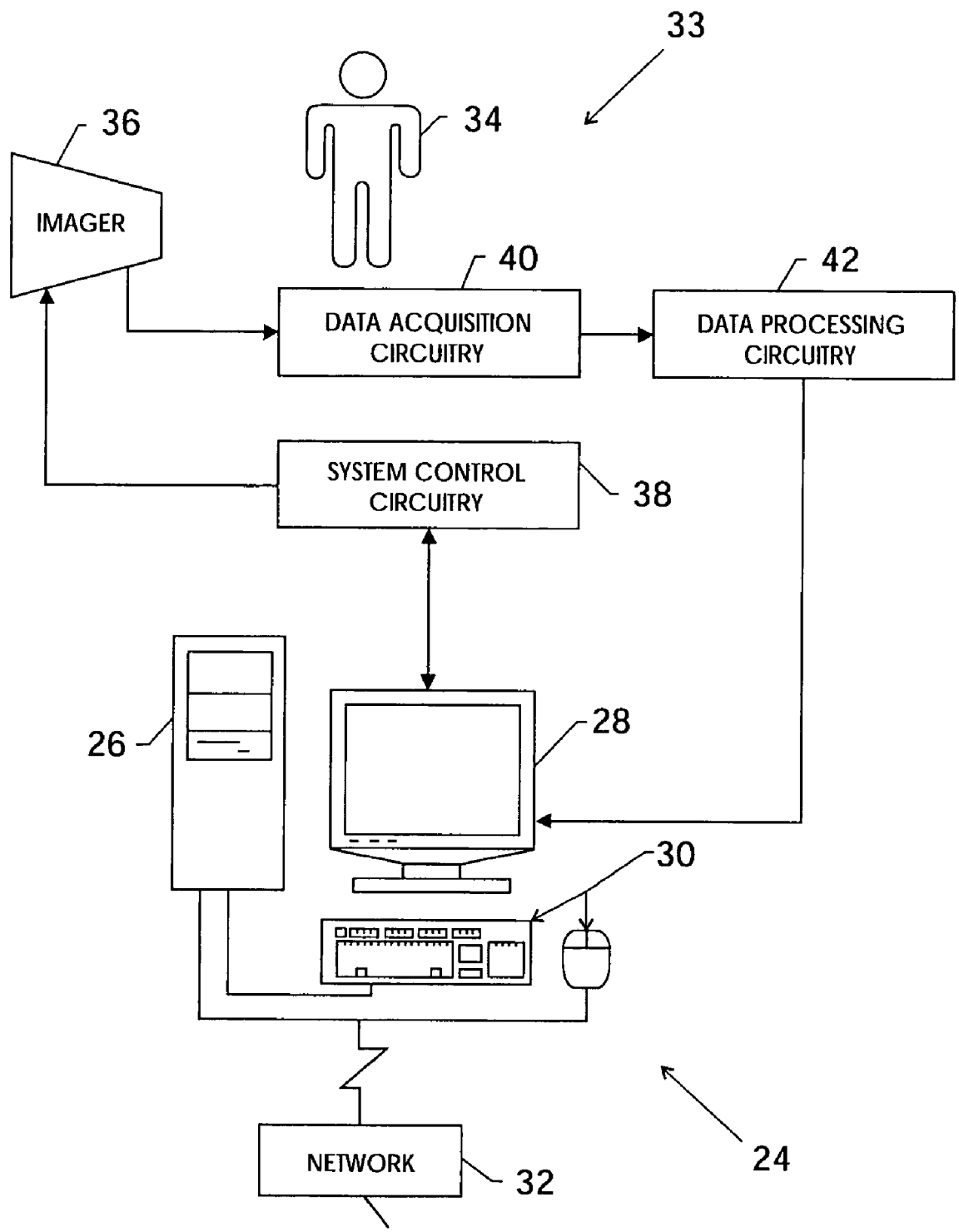
FIG. 2 is a general diagrammatical representation of certain functional components of an exemplary generic imaging system equipped for determining a service interval via the present technique.

In the medical diagnostic context, various imaging resources may be available for diagnosing medical events and conditions in both soft and hard tissue, and for analyzing structures and function of specific anatomies. Moreover, imaging systems are available which can be used during surgical interventions, such as to assist in guiding surgical components through areas which are difficult to access or impossible to visualize. FIG. 2 provides a general overview of an exemplary imaging system, while FIGS. 3 and 4 offer somewhat greater detail into the major system components of certain specific modality systems. Such imaging resources may utilize the present technique for determining service intervals for these devices.

Referring to FIG. 2, an imaging system 33 is depicted. The imaging system 33 may comprise a maintained system 16, 18, or 20 of device group 12. Generally the imaging system 33 includes some type of imager 36, that detects signals and converts the signals to useful data. As described more fully below, the imager 36 may operate in accordance with various physical principles for creating the image data. In general, however, the imager creates image data indicative of regions of interest in a patient 34 either in a conventional support, such as photographic film, or in a digital medium.

The imager operates under the control of system control circuitry 38. The system control circuitry may include a wide range of circuits, such as radiation source control circuits, timing circuits, circuits for coordinating data acquisition in conjunction with patient or table movements, circuits for controlling the position of radiation sources and detectors, and so forth. The imager 36, following acquisition of the image data or signals, may process the signals, such as for conversion to digital values, and forwards the image data to data acquisition circuitry 40. In the case of analog media, such as photographic film, the data acquisition system may generally include supports for the film, as well as equipment for developing the film and producing hard copies that may be subsequently digitized. For digital systems, the data acquisition circuitry 40 may perform a wide range of initial processing functions, such as adjustment of digital dynamic ranges, smoothing or sharpening of data, as well as compiling of data streams and files, where desired. The data is then transferred to data processing circuitry 42 where additional processing and analysis are performed. For conventional media such as photographic film, the data processing system may apply textual information to films, as well as attach certain notes or patient-identifying information. For the various digital imaging systems available, the data processing circuitry perform substantial analyses of data, ordering of data, sharpening, smoothing, feature recognition, and so forth.

Ultimately, the image data is forwarded to some type of operator interface 24 for viewing and analysis. While operations may be performed on the image data prior to viewing, the operator interface 24 is at some point useful for viewing reconstructed images based upon the image data collected. It should be noted that in the case of photographic film, images are typically posted on light boxes or similar displays to permit radiologists and attending physicians to more easily read and annotate image sequences. The images may also be stored in short or long-term storage devices, for the present purposes generally considered to be included within the interface 24, such as picture archiving communication systems. The image data can also be transferred to remote locations, such as via network 32. It should also be noted that, from a general standpoint, the operator interface 24 affords control of the imaging system, typically through interface with the system control circuitry 38. Moreover, it should also be noted that more than a single operator interface 24 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

Figure 3:
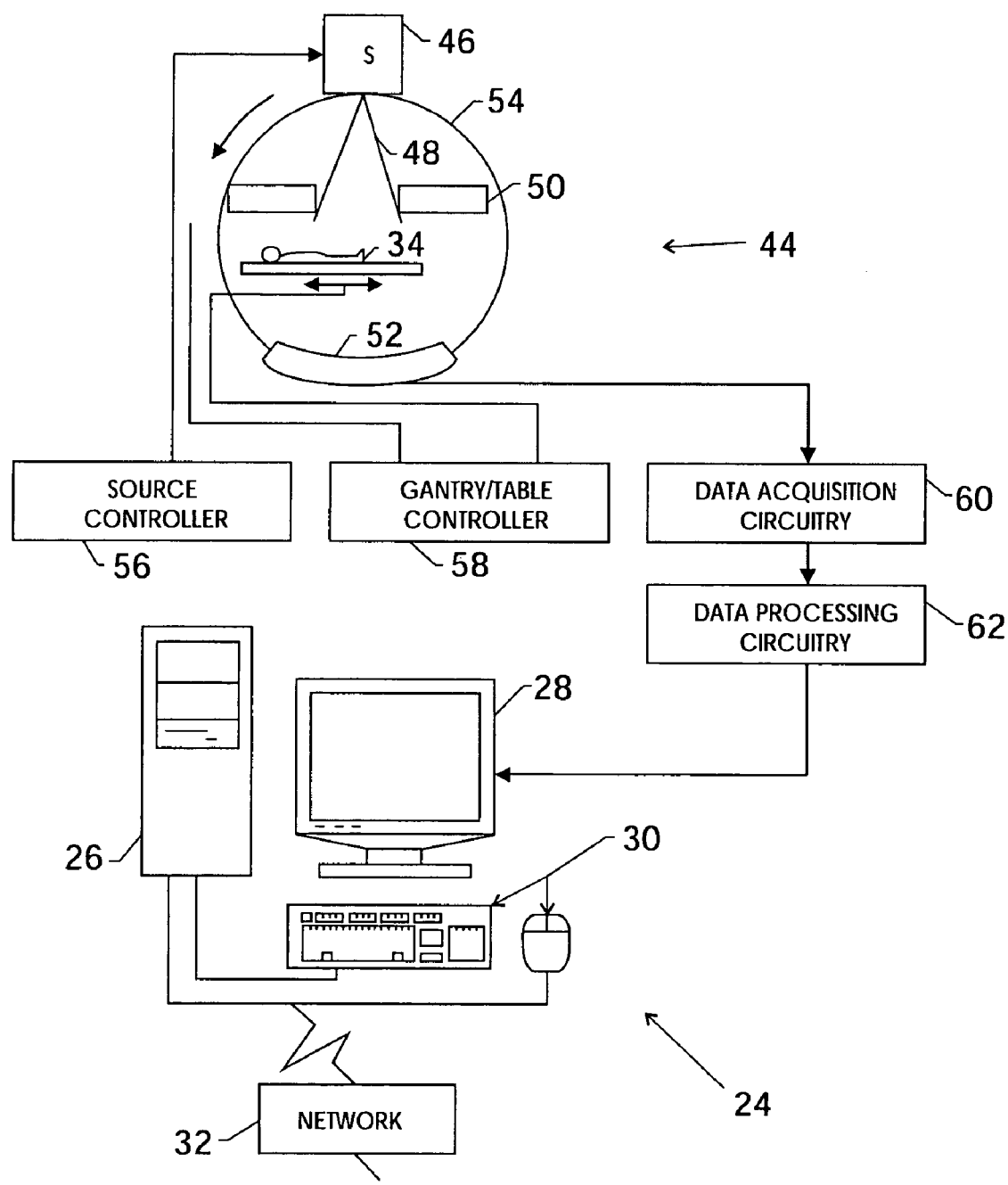
FIG. 3 is a diagrammatical representation of an exemplary computed tomography imaging system equipped for determining a service interval for the system.

A particular example of imaging system 33 is a computed tomography (CT) imaging system 44, the basic components of which are depicted in FIG. 3. The CT imaging system 44 includes a radiation source 46, which is configured to generate X-ray radiation in a fan or cone-shaped beam 48. A collimator 50 defines limits of the radiation beam. The radiation beam 48 is directed toward a detector 52 made up of an array of photodiodes and transistors which permit readout of charges of the diodes depleted by impact of the radiation from the source 46. Radiation source 46, collimator 50 and detector 52 may be mounted on a rotating gantry 54 that enables them to be rotated about a subject, typically at speeds approaching two or more rotations per second. Configurations of CT imaging systems 44 which differ from that depicted in FIG. 3 are also possible, as one of ordinary skill in the art will appreciate. For example, in some configurations detector 52 comprises a ring of detector elements that does not rotate. These and other alternative configurations, such as electron beam tomography (EBT), are well within the scope of the present techniques.

In the depicted configuration, the source and detector are rotated during an examination sequence, generating a series of view frames at angularly displaced locations around a patient 34 positioned within gantry 54. A number of view frames (e.g. between 500 and 1000) are collected for each rotation, and a number of rotations may be made, such as in a helical pattern as patient 34 is slowly moved along the axial direction of system 44. For each view frame, data is collected from individual pixel locations of detector 52 to generate a large volume of discrete data. A source controller 56 regulates operation of radiation source 46, while a gantry/table controller 58 regulates rotation of gantry 54 and control of movement of patient 34.

Data collected by detector 52 is digitized and forwarded to data acquisition circuitry 60. Data acquisition circuitry 60 may perform initial processing of the data, such as for generation of a data file. The data file may incorporate other useful information, such as relating to cardiac cycles, positions within the system at specific times, and so forth. Data processing circuitry 62 then receives the data and performs a wide range of data manipulation and computations.

In general, data from the CT scanner can be reconstructed in a range of manners. For example, view frames for a full 360° of rotation may be used to construct an image of a slice or slab through patient 34. However, because some of the information is typically redundant (imaging the same anatomies on opposite sides of a patient), reduced data sets comprising information for view frames acquired over 180° plus the angle of the radiation fan may be constructed. Alternatively, multi-sector reconstructions are utilized in which the same number of view frames may be acquired from portions of multiple rotational cycles around patient 34. Reconstruction of the data into useful images then includes computations of projections of radiation on detector 52 and identification of relative attenuations of the data by specific locations within patient 34. The raw, the partially processed, and the fully processed data may be forwarded for post-processing, storage and image reconstruction. The data may be available immediately to an operator, such as at an operator interface 24, and may be transmitted remotely via network 32.

Figure 4:
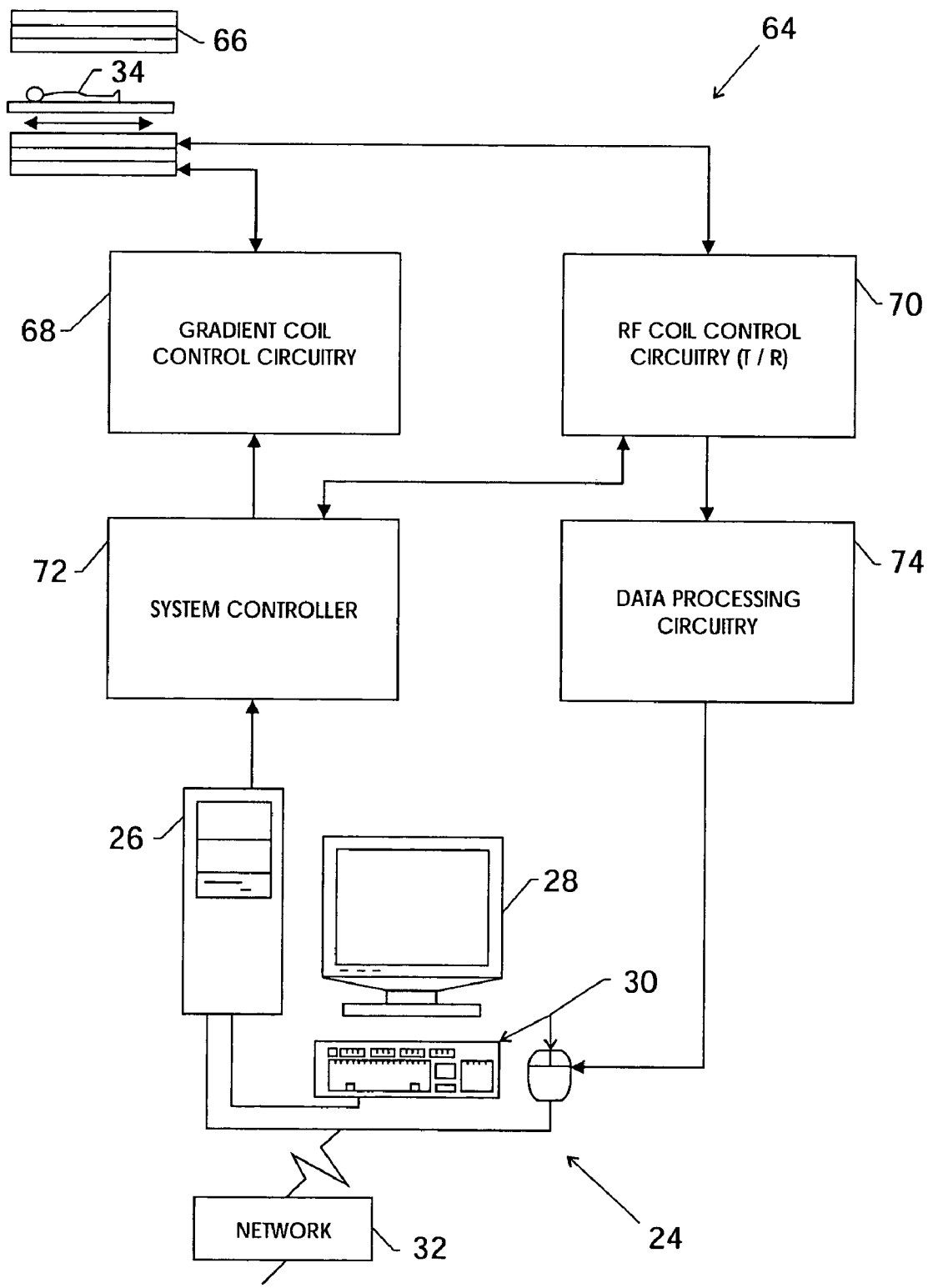
FIG. 4 is a diagrammatical representation of an exemplary magnetic resonance imaging system equipped for determining a service interval for the system.

Another example of an imaging system 33 is a magnetic resonance imaging (MRI) system 64, represented diagrammatically in FIG. 4. System 64 includes a scanner 66 in which a patient 34 is positioned for acquisition of image data. Scanner 66 generally includes a primary magnet for generating a magnetic field that influences gyromagnetic materials within the patient's body. As the gyromagnetic material, typically water and metabolites, attempts to align with the magnetic field, gradient coils produce additional magnetic fields that are orthogonally oriented with respect to one another. The gradient fields effectively select a slice of tissue through the patient for imaging, and encode the gyromagnetic materials within the slice in accordance with phase and frequency of their rotation. A radio-frequency (RF) coil in the scanner generates high frequency pulses to excite the gyromagnetic material and, as the material attempts to realign itself with the magnetic fields, magnetic resonance signals are emitted which are collected by the radio-frequency coil.

Scanner 66 is coupled to gradient coil control circuitry 68 and to RF coil control circuitry 70. Gradient coil control circuitry 68 permits regulation of various pulse sequences that define imaging or examination methodologies used to generate the image data. Pulse sequence descriptions implemented via gradient coil control circuitry 68 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. RF coil control circuitry 70 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

Gradient and RF coil control circuitries 68 and 70 function under the direction of a system controller 72. System controller 72 implements pulse sequence descriptions that define the image data acquisition process. System controller 72 will generally permit some amount of adaptation or configuration of the examination sequence by means of an operator interface 24.

Data processing circuitry 74 receives the detected MR signals and processes the signals to obtain data for reconstruction. In general, the data processing circuitry 74 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. Data processing circuitry 74 may perform a wide range of other functions, such as for image enhancement, dynamic range adjustment, intensity adjustments, smoothing, sharpening, and so forth. The resulting processed image data is typically forwarded to an operator interface 24 for viewing, and/or for short or long-term storage. As in the case of the foregoing imaging systems, MR image data may be viewed locally at a scanner location, or may be transmitted to remote locations both within an institution and remote from an institution such as via network 32.

Figure 5:
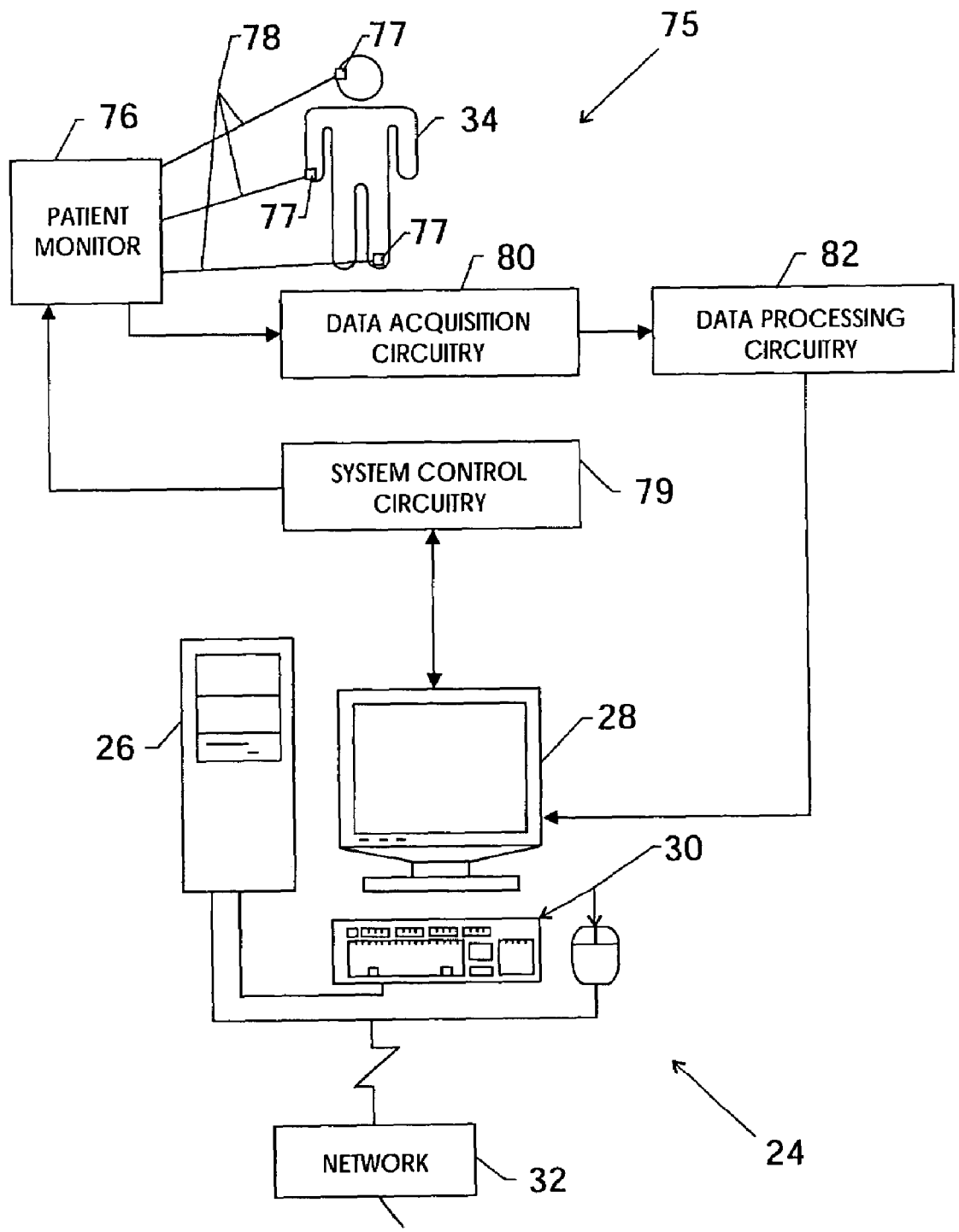
FIG. 5 is a general diagrammatical representation of certain functional components of an exemplary generic patient monitoring system equipped for determining a service interval via the present technique.

Referring to FIG. 5, a patient monitoring system 75, which might comprise one or more of the maintained systems 16, 18, or 20, includes some type of patient monitor 76 that measures vital signs of patient 34. For example, one or more sensor or contact pads 77, such as ECG pads, disposed on patient 34 may be connected to patient monitor 76 via one or more leads 78. Patient monitor 76 operates under the control of system control circuitry 79. System control circuitry 79 may include a wide range of circuits useful for operating patient monitor 76. Patient monitor 76, following acquisition of the patient data or signals, may process the signals and forwards the data to data acquisition circuitry 80. Data acquisition circuitry 80 may perform a wide range of initial processing functions, such as smoothing or sharpening of data as well as compiling of data streams and files, where desired. The data is then transferred to data processing circuitry 82 where additional processing and analysis are performed.

Ultimately, the data is forwarded to an operator interface 24 for viewing and analysis. The data may be stored in any suitable memory device of operator interface 24 or on monitoring system 75. The data may also be transferred to, and stored in, remote locations, such as server 22 (FIG. 1) via network 32. It should also be noted that, from a general standpoint, operator interface 24 affords control of the system, typically through interface with system control circuitry 79. Moreover, it should also be noted that more than a single operator interface 24 may be provided. Additionally, other embodiments may be employed in which any of patient monitor 76, system control circuitry 79, data acquisition circuitry 80, data processing circuitry 82, and operator interface 24 are incorporated into a single device. Such a matter of routine alteration, organization, or incorporation of the physical elements does not change the functionality of the present technique.

Figure 6:
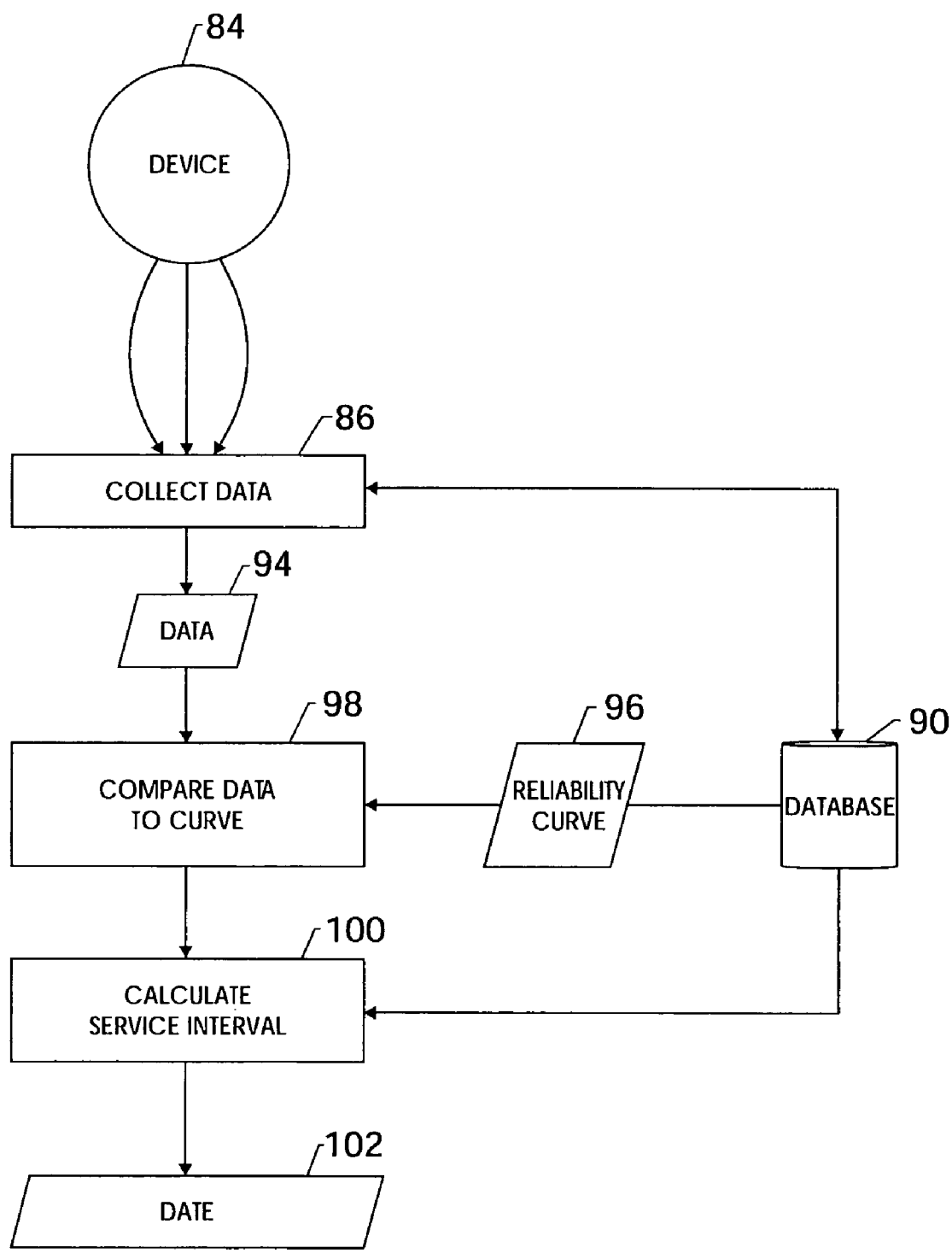
FIG. 6 is a flow chart representing exemplary steps in determining a service interval.

FIG. 6 represents a flowchart demonstrating exemplary steps in determining a service interval implemented by scheduling system 10 in accordance with the present technique. The scheduling system collects data 94 in step 86 from a device 84. The data collected may be operational data, such as that generated by a run time meter, a cycle counter, a continuous system monitor, or a self-test monitor; may be non-operational data, such as the age or the repair history of the device; or may be a combination of the two. Non-operational data may also include qualitative or quantitative measures conveying information about the device location, such as operating environment, i.e., temperature and humidity; traffic and workflow; and/or critical uses, such as deployment in intensive or cardiac care or surgery. Device 84 may be a maintained system 16, 18, or 20 in its entirety or may be a component of such a system, such as an X-ray source 46, a detector 52, control circuitry, an operator interface 24, or a patient monitor 76.

In addition, device related data 94 may be collected from a database 90 or some other remote store of device data. For example, the age of device 84 and data associated with the location of device 84 may be retrieved from database 90. Database 90 may also provide information useful in calculating a service interval and determining a service date. One skilled in the art will recognize that database 90 may actually comprise a plurality of databases capable of providing information to the various steps of the present technique. Database 90 and any variation thereof may be stored within any suitable device, including a computer workstation or server, may be stored within device 84 itself, and/or may be local to or remote from the maintained system 16, 18, or 20.

Figure 7:
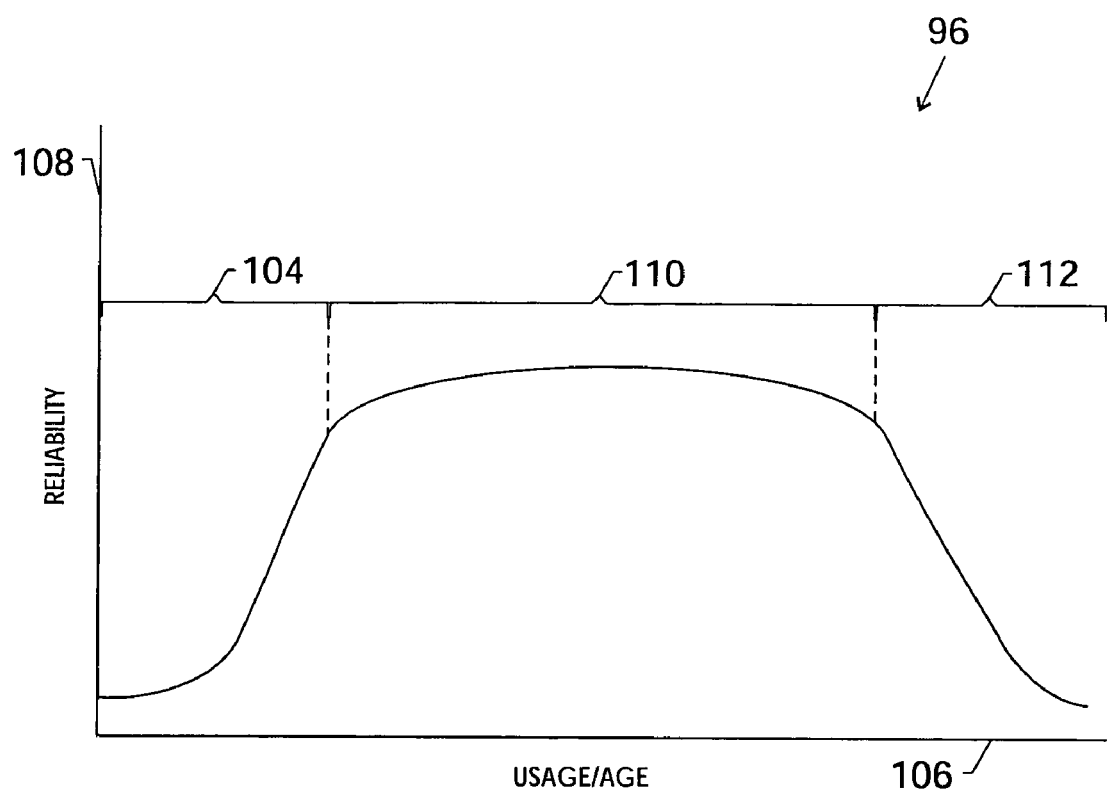
FIG. 7 is a graphical representation of a typical reliability curve that may be employed by the present technique.

The data 94 may be compared, at step 98, to at least one reliability curve 96 which may be supplied by database 90 or another source. A reliability curve 96, such as the curve depicted in FIG. 7, may depict the reliability of a device or component, shown along the vertical axis 108, as a function of its age, shown along horizontal axis 106. When brand new, a device may be unreliable, requiring frequent repair and adjustments to put it in proper working order. Once the device is adjusted to optimal working order, however, it may continue operating for years without need of repair. As the device or component wears, it will eventually require servicing in order to maintain the same degree of reliability and functionality. Reliability curves 96 will of course vary depending on the device 84 being measured. These reliability curves may be representative of a wide range of devices and components, from the most complex of machines to simple pumps or switches.

The comparison of the data 94 and curve 96 may allow the device to be located on reliability curve 96. In this way, the reliability characteristics or profile of device 84 can be determined or estimated based upon the population's known reliability profile, i.e., reliability curve 96. Once device 84 is located on reliability curve 96, a service interval that reflects that knowledge may be calculated at step 100. For example, the service interval for a device 84 located in the early or "burn-in" period 104 of reliability curve 96 would likely be substantially shorter than the interval for a device 84 in the plateau region 110 of reliability curve 96. Similarly, the service interval for a device 84 located in the late or "burn-out" region 112 of the reliability curve 96 would presumably be shorter than the interval for a device 84 in the plateau region 110. In this manner, the service interval for a device 84 may account for the reliability profile of the population of devices such that, when device 84 is at an age or usage level where the population is known to be less reliable, service calls may be performed more frequently. Conversely, a device 84 that is at an age or usage level that is known to correspond to high reliability in the population will receive less frequent service calls.

A possible service interval may be determined for each data source, i.e., the components or subcomponents of device 84, for which data 94 has been collected and for which a reliability curve 96 exists. Alternatively, comparison 98 may be performed for a device 84 or a set of components of device 84 if reliability curve 96 and data 94 are representative of the aggregate behavior. In this manner, the comparison process, and the related service interval calculation, may be as component specific or as general as desired. From the service intervals calculated in this manner as step 100, an optimal service interval may be selected.

As one of ordinary skill in the art will appreciate, the optimal service interval may be calculated in various ways. For example, the optimal service interval may be the shortest interval calculated. Alternatively, the optimal service interval may be the shortest interval calculated adjusted by a fixed or statistically derived time interval, such as by an interval based on a standard error or a standard deviation of the interval. Similarly, the optimal time interval may not be the shortest interval calculated, but may instead be a different calculated interval, such as the second or third shortest interval. The selection of the optimal service interval may be determined or weighted by various factors such as by the criticality of the component to be serviced, the institution's expenditure or maintenance preferences, and/or the presence or absence of clusters of intervals which might be combined, as determined by the preferences of the institution. These factors and others may, alone or in combination, be used in the determination of the optimal service interval. Once determined, the optimal service interval may then be used to determine a service date 102.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for determining a service interval for a device comprising:
   collecting one or more data points regarding a device;
   comparing the one or more data points to at least one associated reliability curve for a population of similar devices;
   calculating a service interval for the device based at least upon the comparison of the one or more data points and the reliability curve; and
   outputting the service interval and selecting an optimal service date based at least in part on the service interval.

2. The method of claim 1, wherein the device comprises medical equipment.

3. The method of claim 2, wherein the medical equipment comprises a patient monitor.

4. The method of claim 2, wherein the medical equipment comprises a diagnostic imaging system.

5. The method of claim 1, wherein the device is a component of a complex machine.

6. The method of claim 1, wherein calculating the service interval comprises evaluating data collected from at least one of:
   a run time meter;
   a cycle counter;
   a continuous system monitor; or
   a self-test monitor.

7. The method of claim 1, wherein at least one reliability curve is derived from a database of repair records for a population of similar devices.

8. The method of claim 1, wherein calculating a service interval is dependent upon at least one of:
   the age of the device;
   the repair history the device;
   the workflow associated with the location of the device;
   the traffic level associated with the location of the device;
   the criticality associated with the device; or
   the environment in which the device operates.

9. The method of claim 1, wherein the one or more data points comprise operational data.

10. The method of claim 1, wherein the one or more data points comprise non-operational data.

11. A method for selecting a service interval from a plurality of service intervals, comprising:
   collecting one or more data points regarding a device from a plurality of data sources;
   calculating a service interval for each data source by at least comparing the one or more data points from the data sources and at least one associated reliability curve; and
   selecting an optimal service interval from the plurality of service intervals.

12. The method of claim 11, wherein the device comprises medical equipment.

13. The method of claim 11, wherein the one or more data points are collected from at least one of:
a run time meter;
a cycle counter;
a continuous system monitor; or
a self-test monitor.

14. The method of claim 11, wherein at least one reliability curve is derived from one or more repair records for a population of similar devices.

15. The method of claim 11, wherein calculating a service interval is dependent upon at least one of:
the age of the device;
the repair history of the device;
the workflow associated with the location of the device;
the traffic level associated with the location of the device;
the criticality associated with the device; or
the environment in which the device is operated.

16. The method of claim 11, wherein the one or more data points comprise operational data.

17. The method of claim 11, wherein the one or more data points comprise non-operational data.

18. A method for determining service intervals for a plurality of devices comprising:
collecting one or more data points regarding a plurality of devices;
calculating a service interval for each device by at least comparing the one or more data points associated with the device and at least one associated reliability curve; and
selecting an optimal service interval for one or more of the devices from the plurality of service intervals.

19. The method of claim 18, wherein at least one of the devices comprises medical equipment.

20. The method of claim 18, wherein at least one of the devices is a component of a complex machine.

21. The method of claim 18, wherein selecting an optimal service interval comprises comparing the service intervals of each device.

22. The method of claim 18, wherein calculating a service interval comprises evaluating data collected from at least one of:
a run time meter;
a cycle counter;
a continuous system monitor; or
a self-test monitor.

23. The method of claim 18, wherein calculating a service interval is dependent upon at least one of:
the age of a device;
the repair history of a device;
the workflow associated with the location of the device;
the traffic level associated with the location of the device;
the criticality associated with the device; or
the environment in which a device operates.

24. The method of claim 18, wherein the one or more data points comprise operational data.

25. The method of claim 18, wherein the one or more data points comprise non-operational data.

26. A system for determining a service interval for a device comprising:
a computer; and
a device connected to the computer through a network, wherein the system is configured to collect one or more data points regarding the device, compare the one or more data points to at least one associated reliability curve for a population of similar devices, calculate a service interval for the device based at least upon the comparison of the one or more data points and the reliability curve, output the service interval, and select an optimal service date based at least in part on the service interval.

27. The system of claim 26, further comprising at least one of:
a run time meter;
a cycle counter;
a continuous system monitor; or
a self-test monitor.

28. The system of claim 26, wherein the computer and the device are networked to a server.

29. The system of claim 28, wherein the server contains reliability data for a population of similar devices.

30. A system for determining a service interval from a plurality of service intervals comprising:
a computer; and
a device connected to the computer through a network, wherein the system is configured to collect one or more data points regarding the device from a plurality of data sources, calculate a service interval for each data source by at least comparing the one or more data points from the data sources and at least one associated reliability curve, and select an optimal service interval from the plurality of service intervals.

31. The system of claim 30, further comprising at least one of:
a run time meter;
a cycle counter;
a continuous system monitor; or
a self-test monitor.

32. The system of claim 30, wherein the computer and the device are networked to a server.

33. The system of claim 32, wherein the server contains reliability data for a population of similar devices.

34. A system for determining service intervals for a plurality of devices comprising:
a computer; and
a plurality of devices connected to the computer through a network, wherein the system is configured to collect one or more data points regarding the plurality of devices, calculate a service interval for each device by at least comparing the one or more data points associated with the device and at least one associated reliability curve, and select an optimal service interval for one or more of the devices from the plurality of service intervals.

35. The system of claim 34, further comprising at least one of:
a run time meter;
a cycle counter;
a continuous system monitor; or
a self-test monitor.

36. The system of claim 34, wherein the computer and the devices are networked to a server.

37. The system of claim 36, wherein the server contains reliability data for populations of similar devices.

38. A system for determining a service interval for a device comprising:
means for collecting one or more data points regarding a device;
means for comparing the one or more data points to at least one associated reliability curve for a population of similar devices;

means for calculating a service interval for the device based at least upon the comparison of the one or more data points and the reliability curve; and means for outputting the service interval and selecting an optimal service date based at least in part on the service interval.

39. A system for determining a service interval from a plurality of service intervals comprising:
means for collecting one or more data points regarding a device from a plurality of data sources;
means for calculating a service interval for each data source by at least comparing the one or more data points from the data sources and at least one associated reliability curve; and
means for selecting an optimal service interval from the plurality of service intervals.

40. A product for determining a service interval for a device comprising:
a computer readable medium configured to store machine executable code; and
a computer program stored on the medium, the program comprising executable routines for collecting one or more data points regarding a device, comparing the one or more data points to at least one associated reliability curve for a population of similar devices, calculating a service interval for the device based at least upon the comparison of the one or more data points and the reliability curve, outputting the service interval, and selecting an optimal service date based at least in part on the service interval.

41. A product for determining a service interval from a plurality of service intervals comprising:
a computer readable medium configured to store machine executable code; and
a computer program stored on the medium, the program comprising executable routines for collecting one or more data points regarding a device from a plurality of data sources, calculating a service interval for each data source by at least comparing the one or more data points from the data sources and at least one associated reliability curve, and selecting an optimal service interval from the plurality of service intervals.

42. A product for determining service intervals for a plurality of devices comprising:
a computer readable medium configured to store machine executable code; and
a computer program stored on the medium, the program comprising executable routines for collecting one or more data points regarding a plurality of devices, calculating a service interval for each device by at least comparing the one or more data points associated with the device and at least one associated reliability curve, and selecting an optimal service interval for one or more of the devices from the plurality of service intervals.

43. A device capable of determining its own service interval comprising:
means for collecting one or more data points regarding a device;
means for comparing the one or more data points to at least one associated reliability curve for a population of similar devices;
means for calculating a service interval for the device based at least upon the comparison of the one or more data points and the reliability curve; and means for outputting the service interval and selecting an optimal service date based at least in part on the service interval.

44. A device capable of determining a service interval from a plurality of service intervals comprising:
means for collecting one or more data points regarding a device from a plurality of data sources;
means for calculating a service interval for each data source by at least comparing the one or more data points from the data sources and at least one associated reliability curve; and
means for selecting an optimal service interval from the plurality of service intervals.

45. A device comprising:
an operator interface unit; and
a processor unit, wherein the processor unit is configured to collect one or more data points regarding a device, compare the one or more data points to at least one associated reliability curve for a population of similar devices, calculate a service interval for the device based at least upon the comparison of the one or more data points and the reliability curve, output the service interval, and select an optimal service date based at least in part on the service interval.

46. The device of claim 45, further comprising at least one of:
a run time meter;
a cycle counter;
a continuous system monitor; or
a self-test monitor.

47. The device of claim 45, wherein the processor is further configured to calculate a service interval based on at least one of:
the age of the device;
the repair history the device;
the workflow associated with the location of the device;
the traffic level associated with the location of the device;
the criticality associated with the device; or
the environment in which the device operates.

48. A device comprising:
an operator interface unit; and
a processor unit, wherein the processor unit is configured to collect one or more data points regarding a device from a plurality of data sources, calculate a service interval for each data source by at least comparing the one or more data points from the data sources and at least one associated reliability curve, and select an optimal service interval from the plurality of service intervals.

49. The device of claim 48, further comprising at least one of:
a run time meter;
a cycle counter;
a continuous system monitor; or
a self-test monitor.

50. The device of claim 48, wherein the processor is further configured to calculate a service interval based on at least one of:
the age of the device;
the repair history the device;
the workflow associated with the location of the device;
the traffic level associated with the location of the device;
the criticality associated with the device; or
the environment in which the device operates.

* * * * *